(12) United States Patent
DeLegge

(10) Patent No.: US 9,763,857 B2
(45) Date of Patent: *Sep. 19, 2017

(54) DEVICE, KIT AND METHOD FOR PLACING JEJUNAL TUBE DEVICE THROUGH STOMACH AND INTO SMALL INTESTINE RELATED APPLICATION

(71) Applicant: DeLegge Medical, Inc., Mt. Pleasant, SC (US)

(72) Inventor: Rebecca L. DeLegge, Mt. Pleasant, SC (US)

(*) Notice: Subject to any disclaimer, the term of this patent is extended or adjusted under 35 U.S.C. 154(b) by 265 days.

This patent is subject to a terminal disclaimer.

(21) Appl. No.: 14/669,368

(22) Filed: Mar. 26, 2015

(65) Prior Publication Data

US 2015/0196461 A1    Jul. 16, 2015

Related U.S. Application Data

(63) Continuation of application No. 13/793,494, filed on Mar. 11, 2013, now Pat. No. 9,028,449.

(60) Provisional application No. 61/638,235, filed on Apr. 25, 2012.

(51) Int. Cl.
  *A61M 5/32*   (2006.01)
  *A61M 31/00*  (2006.01)
  *A61J 15/00*  (2006.01)
  *A61B 17/34*  (2006.01)

(52) U.S. Cl.
  CPC ....... *A61J 15/0069* (2013.01); *A61B 17/3415* (2013.01); *A61J 15/0019* (2013.01)

(58) Field of Classification Search
  CPC ............... A61J 15/0019; A61J 15/0069; A61J 15/0023; A61J 15/0038; A61J 15/0046; A61J 15/0092; A61B 17/3415
  See application file for complete search history.

(56) References Cited

U.S. PATENT DOCUMENTS

| | | | |
|---|---|---|---|
| 4,212,304 A | 7/1980 | Finney | |
| 4,668,225 A * | 5/1987 | Russo | A61J 15/0015 604/104 |
| 5,037,387 A | 8/1991 | Quinn et al. | |
| 5,259,367 A | 11/1993 | Kirby et al. | |
| 5,334,185 A | 8/1994 | Giesy et al. | |
| 5,720,734 A | 2/1998 | Copenhaver et al. | |
| 6,471,676 B1 | 10/2002 | DeLegge et al. | |
| 7,563,254 B2 | 7/2009 | DeLegge | |
| 7,976,495 B2 | 7/2011 | DeLegge et al. | |
| 8,382,770 B2 | 2/2013 | DeLegge et al. | |
| 8,473,034 B2 | 6/2013 | Cage et al. | |
| 8,632,492 B2 | 1/2014 | DeLegge | |
| 8,721,586 B1 | 5/2014 | Rivera et al. | |
| 8,968,248 B2 | 3/2015 | DeLegge et al. | |

(Continued)

*Primary Examiner* — Rebecca E Eisenberg
(74) *Attorney, Agent, or Firm* — B. Craig Killough; Barnwell Whaley Patterson & Helms

(57) ABSTRACT

A device and method for placing a jejunal feeding tube through a stomach and into a small intestine. A mechanism is formed to a shape that contacts walls of the small intestine along a length of the small intestine to grip the walls and anchor the jejunal feeding tube. The mechanism is present on a distal end of the jejunal feeding tube that is present in the small intestine after placement of the jejunal feeding tube. The mechanism is straightened for placement into the small intestine with a stiffening apparatus.

20 Claims, 11 Drawing Sheets

(56) References Cited

U.S. PATENT DOCUMENTS

| | | |
|---|---|---|
| 2003/0171718 A1 | 9/2003 | DeLegge et al. |
| 2007/0167923 A1 | 7/2007 | Deal |
| 2009/0318897 A1* | 12/2009 | Bailey ................ A61J 15/0015 604/537 |
| 2010/0298812 A1 | 11/2010 | Wolkenstorfer |
| 2010/0305503 A1 | 12/2010 | Fang et al. |
| 2012/0226144 A1 | 9/2012 | Cage et al. |

* cited by examiner

DEVICE, KIT AND METHOD FOR PLACING JEJUNAL TUBE DEVICE THROUGH STOMACH AND INTO SMALL INTESTINE RELATED APPLICATION

RELATED APPLICATION

This application is a continuation of application Ser. No. 13/793,494, filed Mar. 11, 2013, which claims the benefit of priority from U.S. Provisional Application No. 61/638,235, filed Apr. 25, 2012, and titled "A Device, Kit and Method for Placing Jejunal Tube Device Through Stomach and Into Small Intestine", the contents of which is incorporated herein by reference.

FIELD OF THE INVENTION

The present invention relates generally to the field of feeding tubes and more specifically to a device and method for placing Jejunal feeding tube devices through stomach and into small intestine.

BACKGROUND OF THE INVENTION

Placement of a Jejunal feeding tube through a previously placed PEG or gastrostomy tube or nasal passage has been difficult at best. The current techniques, such as the wire guide method and the drag and pull method, are full of challenges from both the method and device perspective.

The wire guide technique utilizes an airplug to fit over a 0.035" wire guide that is threaded through a PEG tube and grasped with a biopsy forceps. This method requires that the stomach be filled with air while the endoscope, forceps and wire guide are advanced into the small bowel before the airplug can be removed from the wire guide. Following the airplug removal, a Jejunal feeding tube, also referred to as a jtube, is pushed over the wire guide, through the PEG tube and into place in the small bowel. The forceps holds the distal end of the wire guide within the small bowel during advancement of the jtube. Once the end of the jtube is positioned within the small bowel, the forceps may be uncoupled from the wire guide. Thereafter, the wire guide may be removed from the jtube. The forceps is typically left in place while the endoscope is removed from the patient to help hold the jtube in place while the wire guide is removed.

There are several drawbacks to the wire guide method. For example, during removal of the forceps from the wire guide or jtube, the jtube is often dragged back into the stomach. If this occurs, then the procedure must be restarted. In addition, care must be taken to maintain tension on the wire guide during the placement procedure. If adequate tension is not maintained, then the jtube may inadvertently curl within the stomach during or subsequent to removal of the wire guide.

The grab and pull method for Jejunal tube placement likewise has drawbacks and is often unsuccessful. This technique involves pushing a jtube with a thin line (like fishing line) looped through the end thereof. A snare or biopsy forceps, which is advanced through an endoscope, is used to grasp the line. The endoscope and snare/forceps are then used to drag the jtube down into the small bowel. However, it is often difficult to detach the snare/forceps from the jtube without dislodging or removing the jtube from the small bowel. This is because the snare/forceps and jtube are usually covered with mucous and other biological material, which causes adhesion and friction between these components. In addition, the jtube, which is relatively flexible, will often loop within the stomach subsequent to placement, thereby pulling the end of the jtube out of the small bowel.

The drawbacks and shortcomings of the procedures described above are addressed by the novel devices and methods of the present invention.

SUMMARY OF THE INVENTION

A device and method for placing a jejunal feeding tube through a stomach and into a small intestine is described herein. A mechanism is formed to a shape that contacts walls of the small intestine along a length of the small intestine to grip the walls and anchor the jejunal feeding tube. The mechanism is present on a distal end of the jejunal feeding tube that is present in the small intestine after placement of the jejunal feeding tube. The mechanism is straightened for placement into the small intestine with a stiffening apparatus.

BRIEF DRAWING DESCRIPTION

The drawings constitute a part of this specification and include exemplary embodiments of the present invention. It is to be understood that in some instances various aspects of the invention may be deleted for clarity, or may not be shown to scale to facilitate an understanding of the invention.

The drawings constitute a part of this specification and include exemplary embodiments of the present invention. It is to be understood that in some instances various aspects of the invention may be deleted for clarity, or may not be shown to scale to facilitate an understanding of the invention.

FIGS. 1 to 6 illustrate sequential steps in an exemplary method of the present invention.

FIGS. 7A-C illustrate an exemplary Jejunal feeding to in accordance with the present invention.

DESCRIPTION OF PREFERRED EMBODIMENTS

Figure 1:
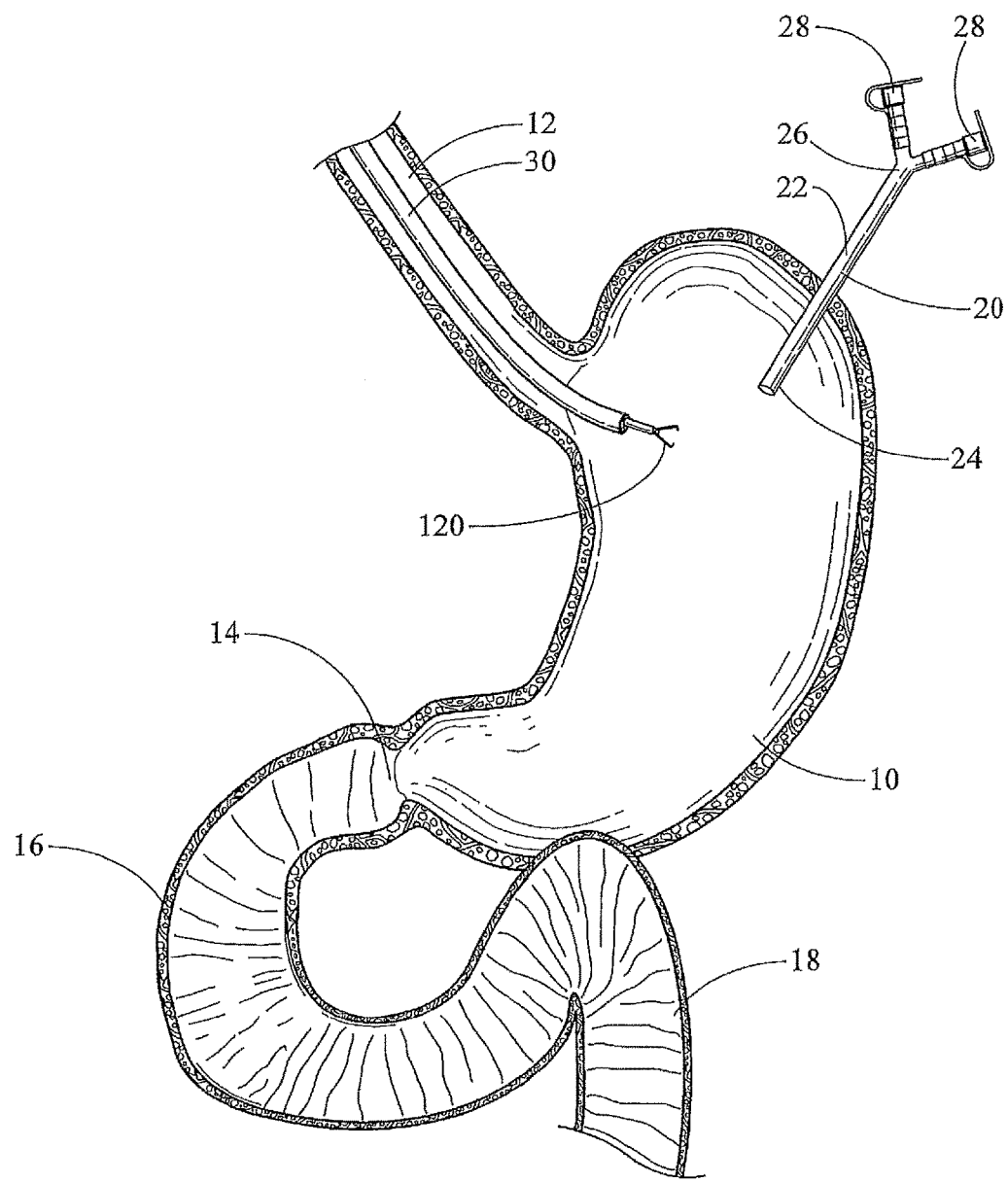

In one embodiment, the present invention includes a jtube that is stiffened with a stiffening apparatus consisting of a stiff catheter with an outer hydrophilic coating and an inner drive wire with a loop configuration disposed on the distal end thereof. The loop is retractable within the jtube, which facilitates disconnection and separation of the loop from a forceps and/or a wire guide. The stiffening apparatus maintains the position of the jtube, and prevents the jtube from looping within the stomach as the endoscope, forceps and/or wire guide are retracted. The stiffening apparatus has an overall length that is slightly longer (for example, approximately 1 centimeter) than the length of the jtube. This allows the stiffener to extend slightly beyond the distal end of the jtube while the jtube is disposed within the stomach. The arrangement ensures that the forceps will be able to securely grasp the end of the stiffening apparatus during the placement procedure.

In one particular embodiment, the stiffening apparatus comprises an elongate mandrel with a loop, which may be a wire or plastic loop, extending distally from a distal end of the mandrel. The mandrel has a length that is shorter (for example, approximately 10 centimeters) than the length of the jtube. This shortened length provides increased flexibility to the distal end portion of the jtube while the stiffening apparatus is disposed therein, which reduces the possibility that the distal end of the jtube will perforate or cause damage to the stomach or small bowel during placement.

In an embodiment, the present invention further includes a c-plug that is adapted to center the jtube within the PEG tube and fill any gaps there between, thereby creating a seal between the jtube and the PEG tube. This enables the stomach to be filled with air, thereby allowing an endoscope and forceps to be used to advance the jtube into the small bowel. The c-plug is removed as the distal end of the jtube is advanced and positioned within the small bowel. The c-plug is separable into two halves to facilitate its removal.

A method of placing a jtube within the small bowel is described. First, the jtube and stiffening apparatus are advanced through an indwelling PEG tube. The c-plug is then positioned and fastened about the jtube and pushed into the PEG tube. Next, the stiffening apparatus is advanced towards the end of the jtube such that the loop, which may be wire or plastic, is extended about 0.5 centimeters beyond the distal end thereof. Under endoscopic viewing, the forceps grasps the loop and pulls the entire mechanism (i.e., the stiffening apparatus and jtube) toward the pylorus. The jtube is then advanced into and positioned within the small bowel. The stiffening apparatus facilitates the placement of the jtube because the increased stiffness of the jtube makes the jtube much easier to drag or push through tissue. Once the jtube is positioned within the small bowel, the endoscope is used to observe the forceps as it is opened and the loop of the stiffening apparatus is retracted into the jtube. The forceps is then retracted from the small bowel. The c-plug is then separated into two halves and removed. The endoscope and forceps are subsequently removed from the small bowel, and the stiffening apparatus is removed from the jtube.

Figure 6:
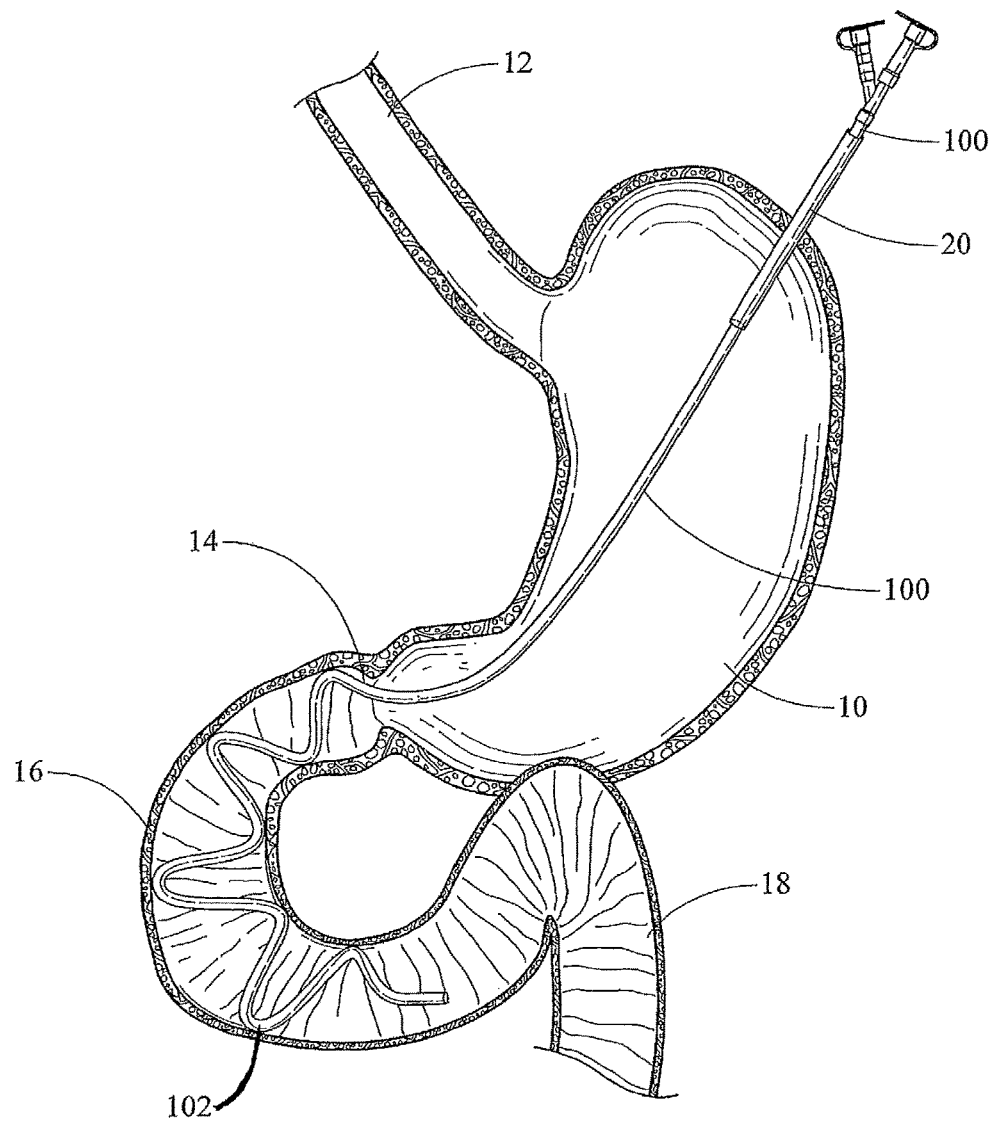

The jtube has a shape at a distal end that is formed to contact the interior walls of the small intestine along a length thereof, and at a plurality of angles, so to engage and anchor the distal end of the feeding tube, and the feeding tube. FIG. 6. In one embodiment, the feeding tube comprises a distal curled end that may provide a spring like mechanism to anchor the jtube within the small bowel. The shape of the mechanism of the distal end of the jtube helps prevent dislodgement during removal of the forceps and stiffening apparatus, and helps prevent dislodgement by a patient inadvertently pulling the jtube out after placement.

The stiffening apparatus may have a means of grasping and pulling the jtube tip. The stiffening apparatus stiffens the jtube during placement procedure. The stiffening apparatus is disposed through a jtube and is extendable therefrom in an embodiment, and is configured to be withdrawn into the jtube to provide a means of separating the feeding tube tip from a grasping device, such as a forceps, without causing dislodgement of said jtube. The stiffening apparatus may have a hydrophilic coating on the outer surface thereof to facilitate removal of the stiffening apparatus from the jtube. The stiffening apparatus may participate to fill the space in within the lumen of the jtube. Eliminating gaps between the jtube and stiffening apparatus enhances support provided by the stiffening apparatus and helps prevent mucus or bodily fluids from entering the jtube during placement.

An embodiment of the present invention provides a c-plug having a means of stabilizing a jtube disposed there through, and further having a means for centering the jtube within a PEG tube while maintaining insufflation of the stomach. The c-plug is also configured to fill the space between a jtube outer diameter and a PEG tube inner diameter. The c-plug may be removable, such as by splitting the device into separate components after use. In one embodiment, the c-plug is comprised of two halves to make a whole device. This allows the c-plug to be removed without having to remove a jtube extending there through.

In accordance with a preferred embodiment of the invention, there is disclosed a device and method for placing Jejunal feeding tube, also referred to as a jtube, through the stomach and into the small intestine comprising: a Jejunal feeding tube having a mechanism that is curled to a diameter that is similar to the diameter of the small bowel, wherein the mechanism may be straightened during placement. An exemplary embodiment of the Jejunal feeding tube is shown in FIGS. 7A-C and 8.

Figure 7A:
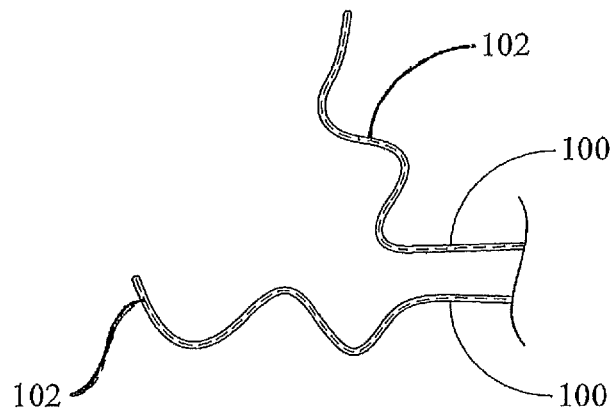
Figure 8:
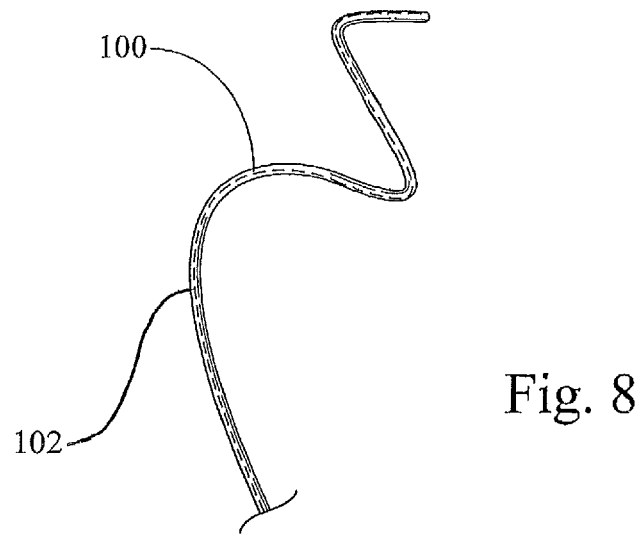
FIG. 8 illustrates the distal end of an exemplary Jejunal tube having a curled or spiral configuration in accordance with the present invention.

FIG. 7A illustrates the distal end portion of a pair of jtubes 100 each having a mechanism 102, which may comprise a wave form, coiled or spiral shape. FIG. 8 illustrates an enlarged view of the mechanism, i.e., the mechanism of the distal end portion 102 of jtube 100. The dimensions of the mechanism is preferably sized to be equal or slightly larger than the inside diameter of the small intestine/bowel to help anchor the distal end portion of the jtube 100 there within. In a coiled or spiral embodiment, the diameter is preferably sized to be equal or slightly larger than the inside diameter of the small bowel.

Figure 7B:
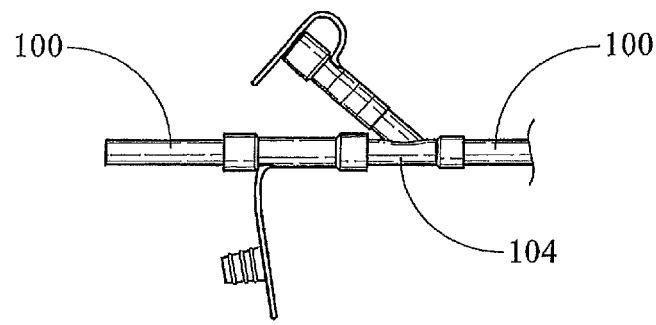

FIG. 7B illustrates the proximal end portion 104 of the jtube 100. In the particular embodiment illustrated, the proximal end portion 104 comprises a pair of ports. One of these ports is configured for the advancement of a stiffening member 110 there through, while the other port is configured for the passage of nutrients or fluids such as saline.

Figure 7C:
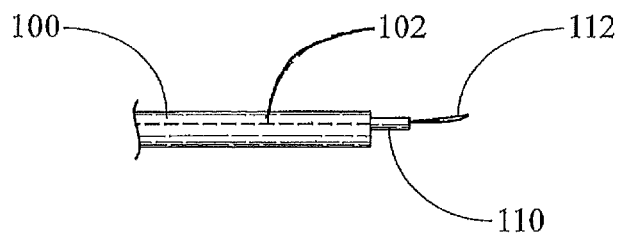

FIG. 7C illustrates the distal end portion of jtube 100 with a stiffening member 110 extending there through. The stiffening member 110 straightens the mechanism 102 to facilitate placement of the jtube 100 into the small bowel. The stiffening member 110 includes a loop or hook 112 on the distal end thereof for grasping by a forceps.

Figure 9:
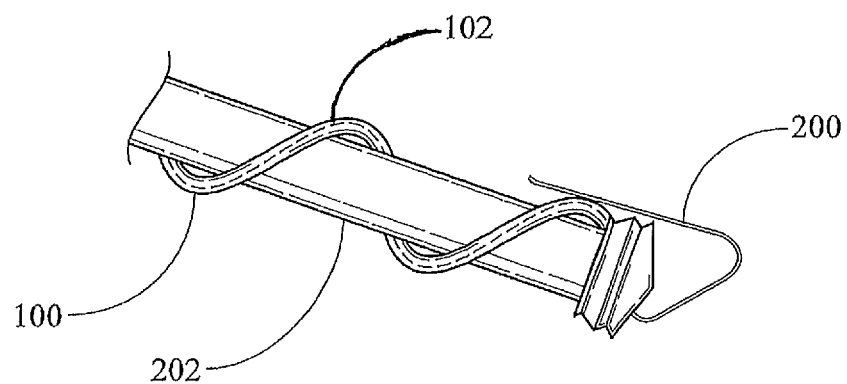
FIG. 9 illustrates a method and system for forming an exemplary Jejunal feeding tube having a curled or spiral configuration in accordance with the present invention.

FIG. 9 illustrates an exemplary method of forming a jtube 100 having a curled or spiral distal end. A forming wire 200 is provided having a spiral shape with the desired pitch and diameter. The forming wire 200 is then inserted into the distal end of the jtube 100 for the desired length. The jtube 100 with forming wire 200 inserted therein is then disposed over a heating element 202. The jtube 100 is then heated sufficiently to set the spiral shape. The forming wire 200 may then be removed. Other methods of forming a spiral shape in the distal end of the jtube 100 are well known in the art.

Figure 10:
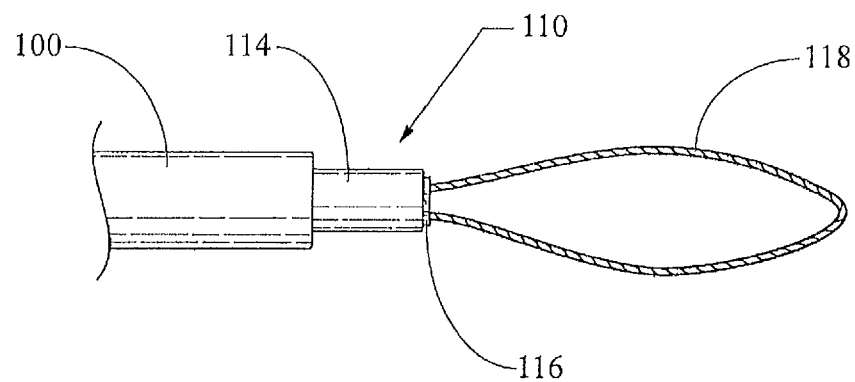
FIG. 10 illustrates the distal end portion of a stiffening apparatus having a retractable loop extending from the distal end of a Jejunal feeding tube in accordance with the present invention.
Figure 11A:
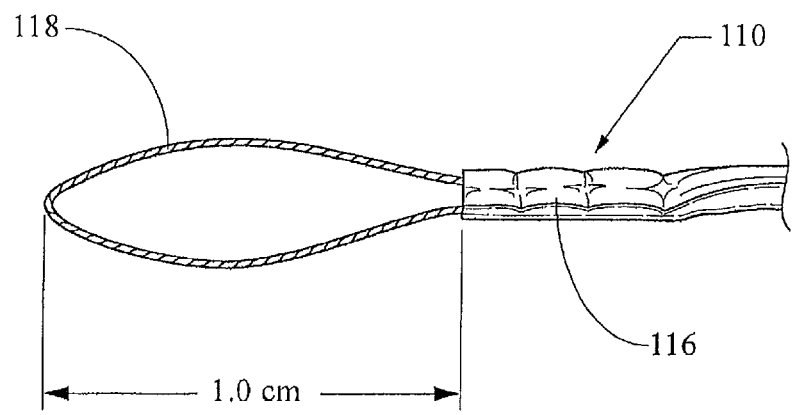
FIG. 11A illustrates distal end portion of a stiffening apparatus having a retractable loop in accordance with the present invention.
Figure 11B:
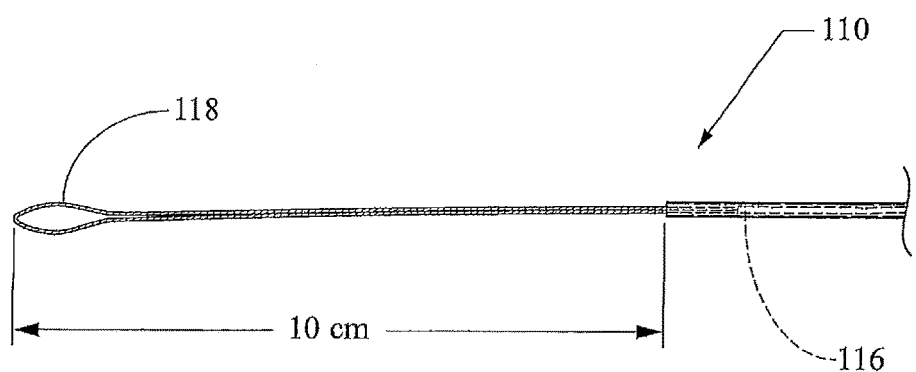
FIG. 11B illustrates an alternative embodiment of a stiffening apparatus having a retractable loop in accordance with the present invention.
Figure 12:
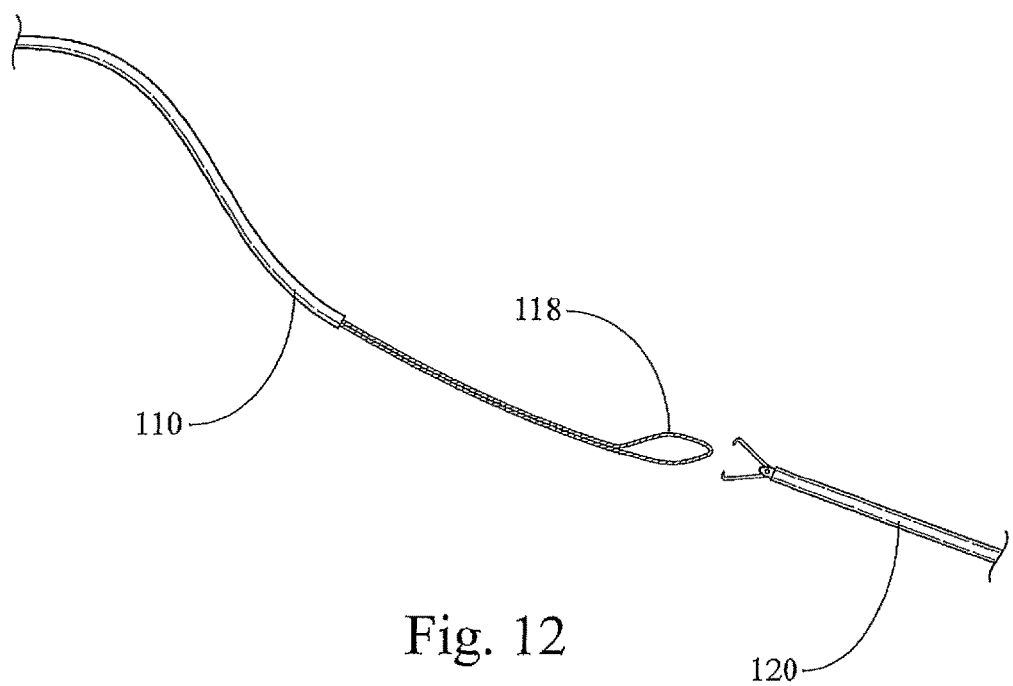
FIG. 12 illustrates a grasping forceps in combination with a stiffening apparatus in accordance with the present invention.

As explained above, the mechanism 102 of the jtube 100 may be straightened with a stiffening apparatus 110 to facilitate placement thereof, wherein the stiffening apparatus is guided by a grasping device such as a forceps. Embodiments of the stiffening apparatus 110 are illustrated in FIGS. 10 and 11A-B. The stiffening apparatus 110 includes a loop 118 affixed to the distal end of a mandrel 116. The loop 118 is configured to be gasped by a forceps 120 (see FIG. 12) during placement of the jtube 100. The mandrel 116 supports the jtube 100 and straightens the mechanism 102 during placement of the jtube 100 within the small bowel.

The overall length of the stiffening apparatus 110, which is the combined length of the mandrel 116 and the loop 118, which may be wire, is longer than the overall length of the jtube 100 such that at least a portion of the loop 118 extends beyond the distal end of the jtube 100, whereby it may be grasped by a forceps or other device. In the preferred embodiment, the length of the stiffening apparatus 110 is configure such that the loop 118 extends approximately 0.5 cm beyond the distal end of the jtube 100 when the stiffening apparatus 110 is fully advanced there through.

In the embodiment illustrated in FIG. 11A, the loop 118 comprises a length of about 0.7 cm to 1 cm. In the embodiment illustrated in FIG. 10B, the loop 118 comprises a length of about 10 cm. Accordingly, the length of the mandrel 116 is shorter for the embodiment of FIG. 11B as compared to the embodiment of FIG. 11A. Because of the shorter length of the mandrel 116 of the embodiment of FIG. 11B, the distal end of the mandrel 116 terminates proximally of the distal end of the jtube 100 when fully advanced there through. This increases the flexibility of the distal end of the jtube 100, thereby reducing the possibility that the distal end of the jtube 100 will puncture or harm tissue during placement thereof. The increased flexibility also facilitates advancement of the jtube 100 into and through the pylorus and reduces the chance of perforation.

As best seen in FIG. 10, the stiffening apparatus 110 may include a catheter 114 disposed over the mandrel 116. The catheter 114 increases the diameter of the stiffening apparatus 110 to more closely match the inside diameter of the jtube 100. This may help to prevent or limit contamination of the jtube 100 during placement. The catheter 114 may also be used to increase, decrease or otherwise alter the stiffness of the stiffening apparatus 100. For example, during placement of the jtube 100 it may be necessary to increase the flexibility of the distal end of the jtube 100. This may be accomplished by retracting catheter 114 relative to the stiffening apparatus 110 and jtube 100. Likewise, catheter 114 may be advanced relative to these components to increase stiffness. Catheter 114 may also be used to assist in separating a forceps from the loop 118 by advancing the catheter 114 over and past the distal end of the loop 118.

In the preferred embodiment, the stiffening apparatus 110 comprises a hydrophilic coating. The hydrophilic coating may be applied to the exterior surface of the mandrel 116 and/or the catheter 114. The hydrophilic coating helps to prevent the stiffening apparatus 110 from dislodging the jtube 100 during removal.

Figure 13:
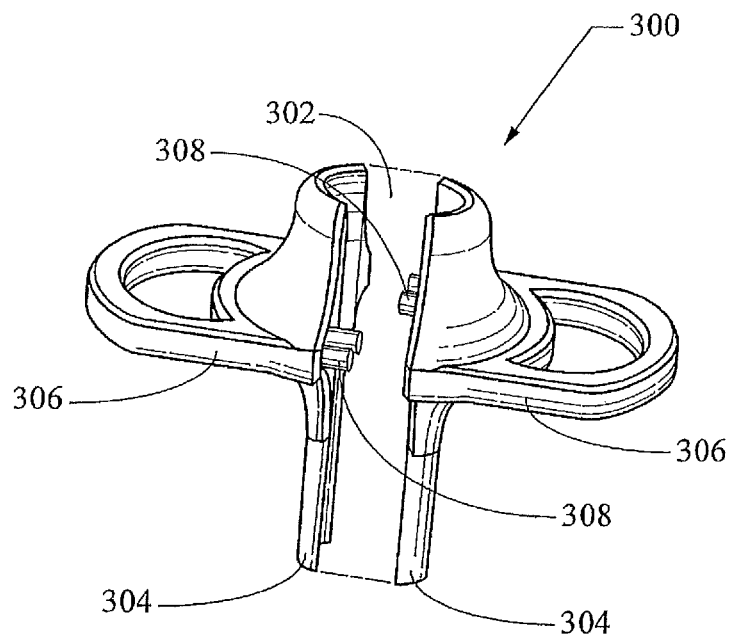
FIG. 13 illustrates a c-plug in accordance with the present invention in an open or separated position.
Figure 14:
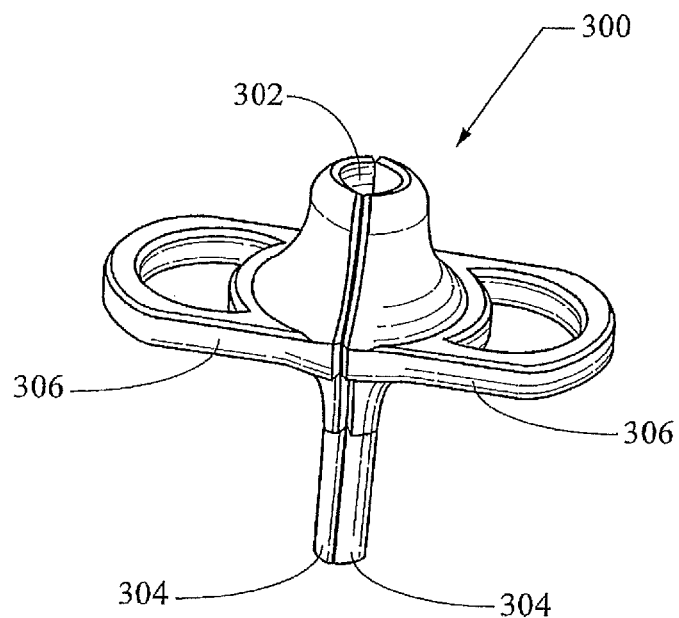
FIG. 14 illustrates a c-plug in accordance with the present invention in a closed or connected position.

Also disclosed is a c-plug for centering the Jejunal feeding tube (jtube) during the placement procedure. An exemplary embodiment of the c-plug 300 is shown in FIGS. 13-14. The c-plug 300 includes a lumen 302 through which a jtube may be advanced. The lumen 302 of the c-plug 300 has an inner diameter that is configured to accommodate a jtube there through, and is preferably configured to seal about the jtube so as to maintain insufflation of the stomach. The c-plug 300 also includes a distal tubular member 304 having an outer diameter that is configured for insertion into a PEG tube (not shown), and is preferably configured to form a seal therewith.

In exemplary embodiment illustrated, the c-plug 300 comprises two separable halves 306 to allow the c-plug 300 to be laterally removed after jtube placement. As illustrated in FIG. 13, each halve 306 may include a mating elements 308 to align and secure the halves 306 together. The ability to separate the c-plug 300 into two components or halves 306 facilitates removal of the c-plug from the PEG tube and jtube.

An exemplary method of placing a Jejunal feeding tube in accordance with the present invention is illustrated in FIGS. 1-6. FIG. 1 illustrates a portion of the gastrointestinal system of a mammalian patient comprising a stomach 10, esophagus 12, pylorus 14, duodenum 16 and jejunum or small intestine (small bowel) 18. A gastrostomy or PEG tube 20 of conventional construction is percutaneously inserted into the stomach 10. The PEG tube 20 comprises a tubular member 22 having a distal end 24 disposed within the stomach 10, and one or more feeding lumens extending there through. The proximal end 26 of the PEG tube 20 comprises connectors 28 adapted to connect to a nutrient supply source, such as an IV set or syringe. The connectors 28 typically include caps to close the connectors 28 when not in use and to prevent contamination thereof. FIG. 1 also illustrates an endoscope 30 being advance through the esophagus 12 and into the stomach 10. A grasping device, such as forceps 120, is shown extending distally from the distal end of the endoscope 30.

Figure 2:
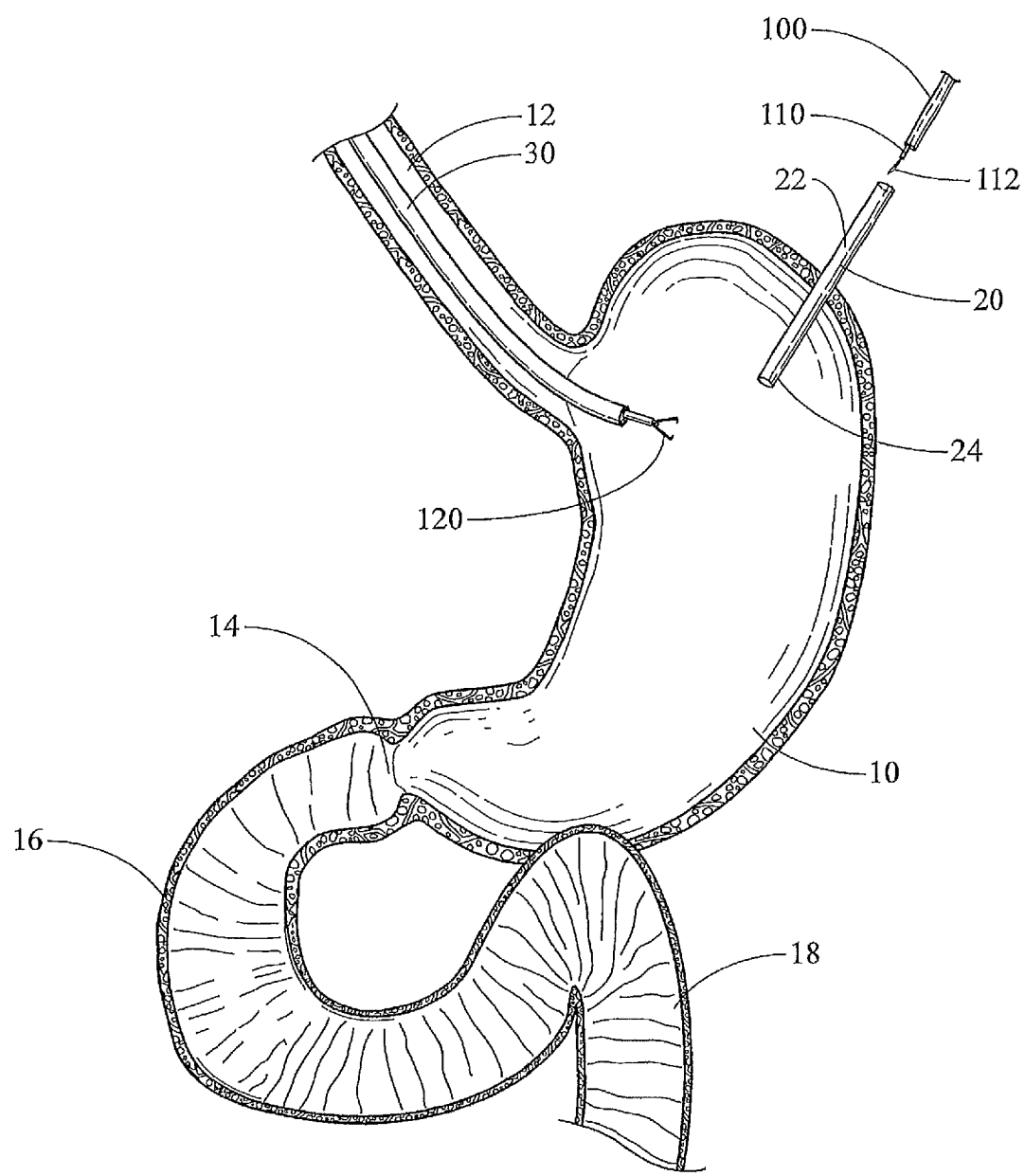

FIG. 2 illustrates the step of advancing a Jejunal feeding tube (jtube) into and through the PEG tube 20. In the preferred embodiment illustrated, the jtube 100 is of the type illustrated in FIGS. 7A-8 and includes a stiffening apparatus 110 disposed there through. The stiffening apparatus 110 is generally of the type illustrated in FIGS. 10-11B, and has been advanced through the jtube 100 a sufficient distance so as to extend the loop 112, which may be wire, beyond the distal end of the jtube 100. Prior to inserting the jtube 100 into the PEG tube 20, the proximal end 26 and connectors 28 of the PEG tube may be cut and removed therefrom. Alternatively, the proximal end 2 and connectors 28 may be retained and the jtube 100 may be advance through one of the connectors 28.

Figure 3:
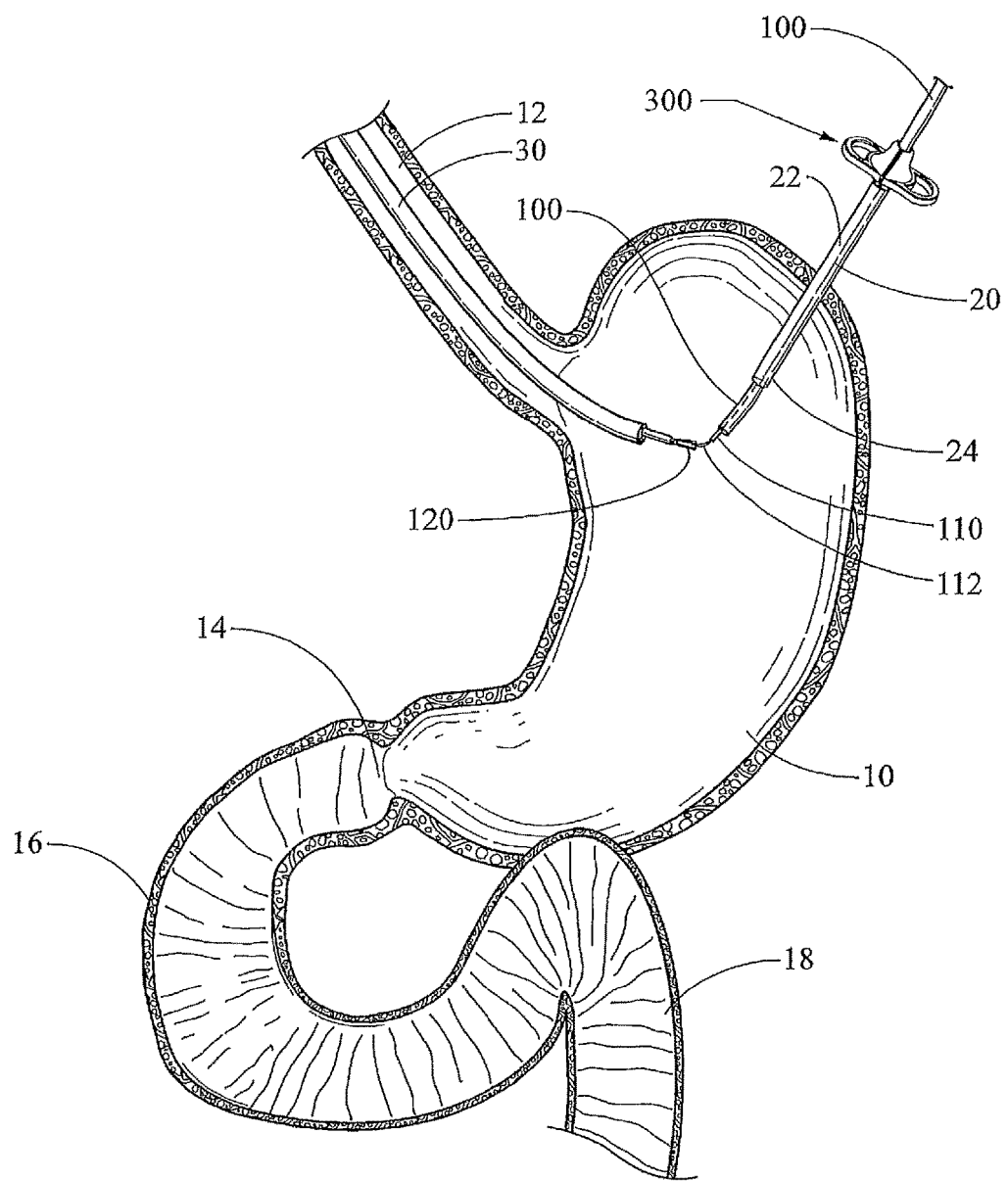

FIG. 3 illustrates the distal end of the jtube 100 extending distally of the distal end 24 of the PEG tube 20 and into the stomach 10. A c-plug 300 of the type illustrated in FIGS. 13-14 is subsequently disposed about the jtube 100 and inserted to the lumen of the PEG tube 20 to thereby create a seal between these components. The stomach 10 is then insufflated to enable the endoscope 30 to view the loop 112 of the stiffening apparatus 110, and to enable the loop 112 to be grasped by the forceps 120.

Figure 4:
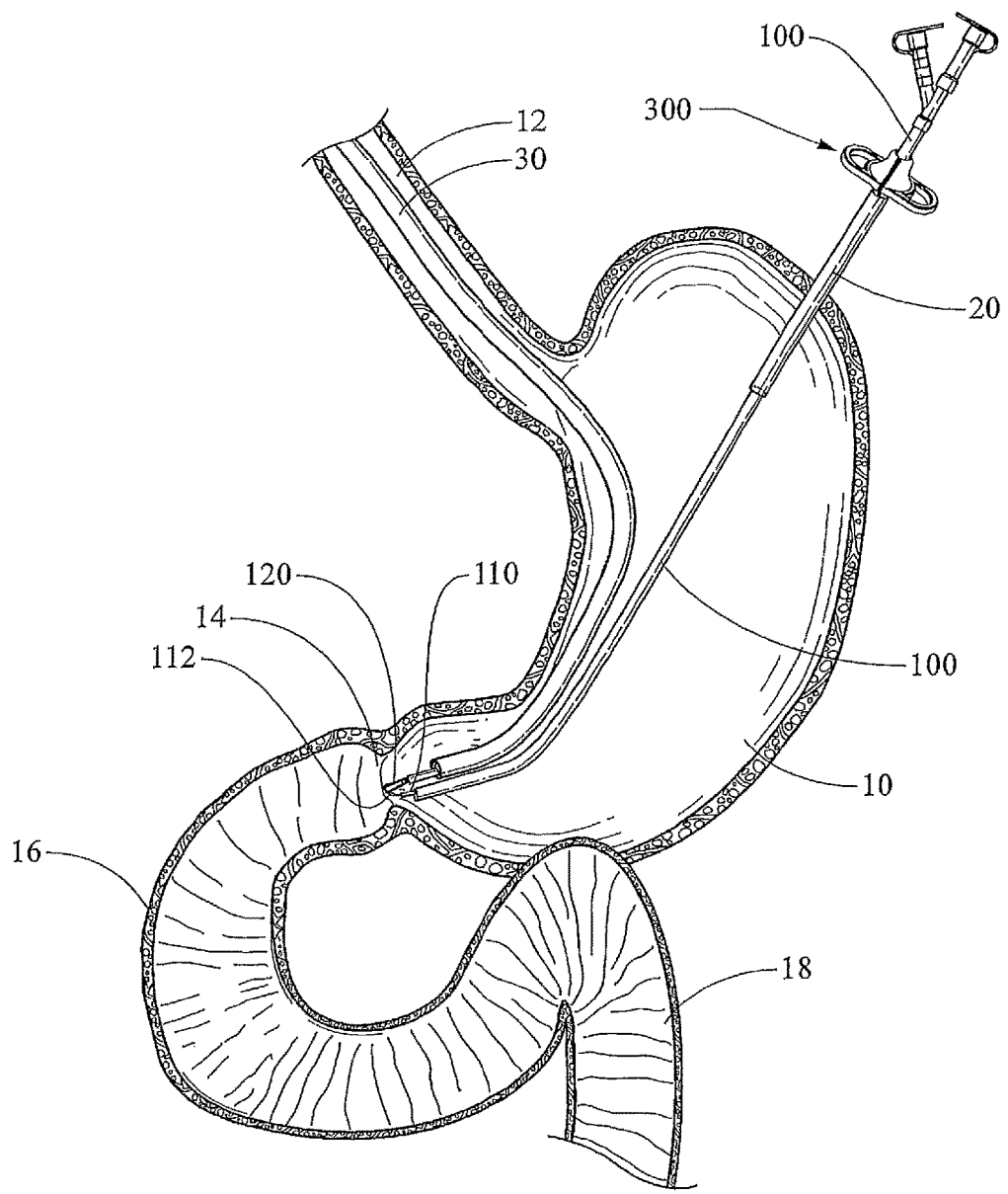

FIG. 4 illustrates the jtube 100 being dragged by the endoscope 30 and forceps 120 towards into the pylorus 14 and towards the duodenum 16. If necessary, the flexibility of the stiffening apparatus 110 may be altered to facilitate advancement thereof by, for example, retracting catheter 114 of the stiffening member 110 (see FIG. 10) proximally to increase the flexibility of the distal end portion of the jtube 100.

Figure 5:
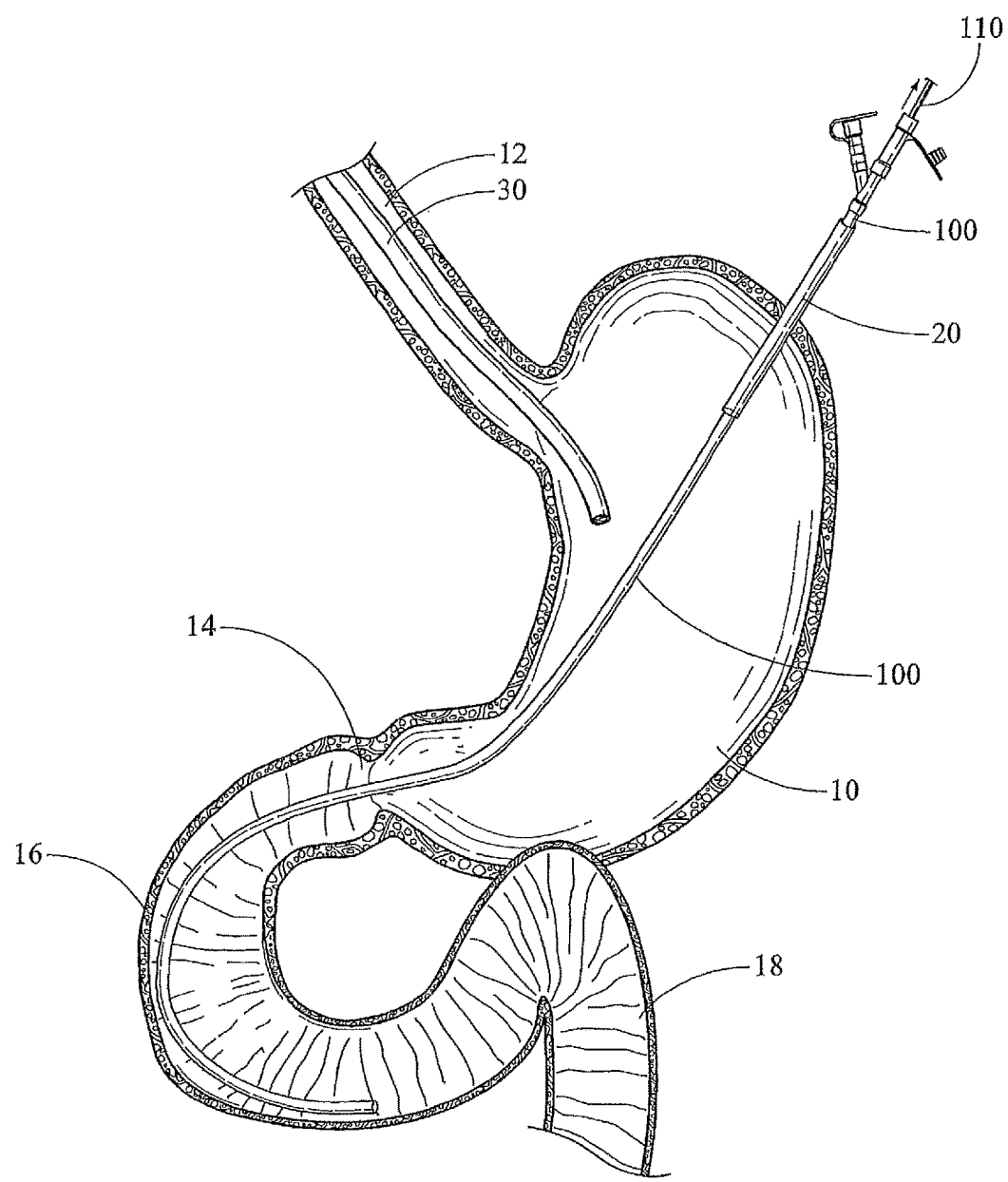

FIG. 5 illustrates the jtube 100 advanced through the pylorus 14 and into the small bowel 18. The forceps 120 is disconnected from the loop 112 of the stiffening apparatus and removed. In the preferred method, the jaws of the forceps 120 are opened while the stiffening apparatus 110 is withdrawn proximally to retract the loop 112 into the lumen of the jtube 100. This causes complete separation of the jaws of the forceps 120 from the loop 112. Alternatively, the catheter 114 of the stiffening apparatus 100 (see FIG. 10) can be advanced distally beyond the distal end of the loop 112 to separate the loop 112 from the forceps 120. The stiffening apparatus 110 is remains disposed within the jtube 100 to provide support thereto and prevent the jtube 100 from becoming dislodged from the small bowel 18. The endoscope 30 and the c-plug 300 can be removed.

FIG. 6 illustrates the jtube 100 in its final position within the small bowel. First, the stiffening apparatus 110 is partially retracted in a proximal direction a sufficient distance to allow the mechanism 102 on the distal end of the jtube 100 to assume its native configuration, the mechanism having shape memory properties. The mechanism 102 anchors the distal end of the jtube 100 within the small bowel 18 by contacting the walls of the small bowel, and by contacting opposing surfaces of the walls of the small bowel, along a length of the small bowel where the mechanism is positioned. Once the jtube 100 is properly anchored, the stiffening member 110 may be completely removed therefrom, wherein the mechanism is in its native configuration, such as that shown in FIG. 6.

In one embodiment, the mechanism contacts a first surface of the wall of the small intestine and subsequently contacts an opposing wall surface of the small intestine further along the length of the small intestine before again contacting the first surface of the wall of the small intestine still further along the length of the small intestine. This pattern may be repeated. The native geometric configuration is therefore not linear, or formed in a large arc, but rather is a shape that will contact the small intestine at opposite sides so as to retard the mechanism from being inadvertently pulled from the small intestine. Examples of shapes of the mechanism that will accomplish this goal of the invention are an undulating shape, a plurality of angles formed in the mechanism that may be 45° to 105°, a coil or a spiral.

In some preferred embodiments, the mechanism is formed in a shape like a wave. As shown in FIG. 6, the wave shape has crests and troughs, and wavelengths. The top of the crest contacts a side of the small intestine, and the bottom of the trough contacts the opposite side. This wave pattern may be repeated as shown in the drawings. The alternating contact of the wave with the small intestine tends to hold or anchor the mechanism in the small intestine, and retard the feeding tube from being pulled out of position.

The wave shape of the mechanism may lie within a plane, that is, the mechanism is substantially flat (while still providing a lumen and conduit for nutrition) and formed as a wave shape. Alternatively, as discussed herein, the wave shape may be a spiral. Further, the wave shape may be three dimensional, with the mechanism neither being substantially flat nor a spiral, but providing the crests and troughs of waves. The wavelength is preferred to average not less than 2 cm, with a space formed between each wave that is preferred to be a minimum of 1 cm. The crests and troughs contact the small intestine along a sufficient length of the small intestine as disclosed herein. The crests and troughs contact the small intestine along a sufficient length of the small intestine to anchor the tube as disclosed herein. A sufficient number of wave shapes is formed and positioned along a length of the small intestine to retard the tube from being inadvertently pulled out. In one embodiment, at least three complete waves are preferred to form the mechanism 120. The individual wave lengths may vary, and a plurality of individual waves may be contiguous to form the mechanism. A length of 5 cm to 50 cm for the mechanism, when straightened, is preferred, and a length of 12 cm to 30 cm is more preferred for most applications.

An exemplary step-by-step method of placing a Jejunal feeding tube in accordance with the present invention is set forth as follows:

1. Scope Patient;
2. Flush the port and lumen of the Jejunal feeding tube (jtube) with sterile water;
3. Insert the stiffening apparatus through the port and into the lumen of the jtube;
4. Advance the stiffening apparatus through the lumen of the jtube sufficiently to extend the loop of the stiffening apparatus beyond the distal end of the jtube;
5. Lubricate the exterior surface of the jtube;
6. Remove the loading adaptor from the jtube;
7. If placing through a PEG tube, load the c-plug onto the jtube, and then slide jtube and PEGJ and c-plug into the PEG tube;
8. Re-inflate the stomach;
9. Advance the forceps through the scope channel of the endoscope and into the stomach;
10. Grasp the loop of the stiffening apparatus with the forceps;
11. Maintain the forceps, stiffening apparatus and jtube close to the end of endoscope to ease guidance thru the pylorus;
12. Push the endoscope (and forceps, stiffening apparatus and jtube) into and through the duodenum, i.e., beyond the duodenal c loop until straight portion of the small bowel is seen;
13. While viewing with the endoscope, advance the forceps, stiffening apparatus and jtube towards the small bowel (Jejunum);
14. Remove the c-plug and continue advancing forceps, stiffening apparatus and jtube until J adapter (connector) of the jtube seats into PEG tube (external);
15. Release the loop of the stiffening apparatus from the forceps and slowly remove the forceps from the endoscope and patient;
16. Observe with the endoscope and verify that the jtube has maintained its position and has not been dislodged by the removal of the forceps;
17. Withdraw the endoscope so as to position the distal end thereof within the stomach;
18. Remove the stiffening apparatus from the jtube;
19. Observe with the endoscope and verify that the jtube has not become dislodged or coiled within stomach; and
20. Remove the endoscope completely from the patient.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed:

1. A kit for placing a jejunal feeding tube through a stomach and into a small intestine of a patient, the kit comprising:
   A jejunal feeding tube comprising a tubular member extending from a proximal end to a distal end, a lumen extending through the tubular member, the proximal end comprising a connector configured for attachment to a source of nutrients, the distal end comprising a mechanism, the mechanism constructed and arranged to contact opposing surfaces of walls of the small intestine along a length of the small intestine and to anchor the jejunal feeding tube in the small intestine by contact with opposing surfaces of walls of the small intestine along a length of the small intestine; and
   an elongate stiffening apparatus removably disposed through the lumen of the tubular member, the elongate stiffening apparatus constructed and arranged to temporarily straighten the mechanism of the jejunal feeding tube when the elongate stiffening apparatus is disposed through the lumen of the tubular member to the distal end of the tubular member.

2. A kit for placing a jejunal feeding tube through a stomach and into a small intestine of a patient as described in claim 1, the kit further comprising:
   a c-plug removably disposed about the jejunal feeding tube, the c-plug configured to provide a seal between the jejunal feeding tube and a percutaneous endoscopic gastrostomy feeding tube when the jejunal feeding tube is disposed through a lumen of the percutaneous endoscopic gastrostomy feeding tube, the c-plug comprising a tubular extension having an outer diameter configured to fit into the lumen of the PEG feeding tube, the tubular extension having an inner diameter configured to fit around the tubular member of the jejunal feeding tube.

3. A kit for placing a jejunal feeding tube through a stomach and into a small intestine of a patient as described in claim 2, wherein the c-plug is separable into two halves to permit lateral removal from the jejunal feeding tube.

4. A kit for placing a jejunal feeding tube through a stomach and into a small intestine of a patient as described in claim 1, wherein the mechanism comprises a plurality of coils and wherein the stiffening apparatus is configured to temporarily straighten the coils of the mechanism.

5. A kit for placing a jejunal feeding tube through a stomach and into a small intestine of a patient as described in claim 1, wherein the mechanism is formed in a spiral and wherein the stiffening apparatus is configured to temporarily straighten the spiral of the mechanism.

6. A kit for placing a jejunal feeding tube through a stomach and into a small intestine of a patient as described in claim 1, wherein the mechanism is formed in a geometric shape to contact a first surface of the wall of the small intestine and subsequently contact an opposing wall surface of the small intestine further along the length of the small intestine before again contacting the first surface of the wall of the small intestine still further along the length of the small intestine, and wherein the stiffening apparatus is configured to temporarily straighten the geometric shape of the mechanism.

7. A kit for placing a jejunal feeding tube through a stomach and into a small intestine of a patient as described in claim 1, wherein the mechanism is formed in the shape of a wave.

8. A kit for placing a jejunal feeding tube through a stomach and into a small intestine of a patient as described in claim 1, wherein the mechanism comprises an overall length when straightened of between 5 centimeters to 30 centimeters.

9. A kit for placing a jejunal feeding tube through a stomach and into a small intestine of a patient as described in claim 1, wherein the mechanism comprises between 1 and 4 spirally shaped coils.

10. A kit for placing a jejunal feeding tube through a stomach and into a small intestine of a patient as described in claim 1, wherein the mechanism is transformed from a straightened configuration when the stiffening apparatus is disposed there through, to a configuration that is a constructed and arranged to contact opposing surfaces of walls of the small intestine along a length of the small intestine and to anchor the jejunal feeding tube in the small intestine when the stiffening apparatus is not disposed there through.

11. A kit for placing a jejunal feeding tube through a stomach and into a small intestine of a patient as described in claim 1, further comprising a loop extending beyond the distal end of the tubular member when the elongate stiffening apparatus is disposed through the lumen of the tubular member, the loop configured to be grasped by a grasping device.

12. A kit for placing a jejunal feeding tube through a stomach and into a small intestine of a patient as described in claim 11, wherein the loop has a length of between 1 cm and 10 cm.

13. A kit for placing a jejunal feeding tube through a stomach and into a small intestine of a patient as described in claim 1, wherein a mandrel of the stiffening apparatus comprises a length that is less than the length of the tubular member of the jejunal feeding tube.

14. A kit for placing a jejunal feeding tube through a stomach and into a small intestine of a patient as described in claim 1, wherein the stiffening apparatus further comprises a catheter movably disposed about a mandrel.

15. The kit according to claim 1 wherein the stiffening apparatus comprises an overall length that is about 0.5 cm to 1.5 cm greater than an overall length of the jejunal feeding tube.

16. A kit for placing a jejunal feeding tube through a stomach and into a small intestine of a patient as described in claim 1, wherein the stiffening apparatus comprises a hydrophilic coating disposed on an outer surface thereof.

17. A kit for placing a jejunal feeding tube through a stomach and into a small intestine of a patient as described in claim 1, wherein the mechanism is formed in a plurality of wave shapes, each having a crest and a trough, and wherein the crest of a first wave of the plurality of waves is spaced at least 2 centimeters from a second wave of the plurality of waves.

18. A method of placing a jejunal feeding tube into a small intestine of a patient, the method comprising the steps of:
   providing a jejunal feeding tube comprising a tubular member extending from a proximal end to a distal end, a lumen extending through the tubular member, the proximal end comprising a connector configured for attachment to a source of nutrients, the distal end comprising a mechanism, the mechanism constructed and arranged to contact opposing surfaces of walls of the small intestine along a length of the small intestine and to anchor the jejunal feeding tube in the small intestine;

providing an elongate stiffening apparatus comprising a loop disposed on a distal end thereof;

disposing the stiffening apparatus through the tubular member of the jejunal feeding tube such that the loop extends distally beyond the distal end of the tubular member, and such that the stiffening apparatus temporarily straightens the mechanism of the jejunal feeding tube;

advancing the jejunal feeding tube and stiffening apparatus into the patient's stomach;

grasping the loop of the stiffening apparatus;

dragging the stiffening apparatus and jejunal feeding tube into the patient's small intestine;

retracting the stiffening apparatus in a proximal direction relative to the jejunal feeding tube until the loop is fully disposed within the feeding lumen of the jejunal feeding tube; and removing the stiffening apparatus from the jejunal feeding tube.

19. The method according to claim 18, further comprising the step of removably disposing a c-plug disposed about the jejunal feeding tube and inserting the c-plug into a PEG feeding tube so as to provide a seal between the jejunal feeding tube and the PEG feeding tube prior to the step of grasping the loop of the stiffening apparatus with the forceps.

20. The method according to claim 19, further comprising the subsequent step of separating the c-plug into a plurality of components and laterally removing the components from the jejunal feeding tube.

* * * * *